(12) United States Patent
Weischedel

(10) Patent No.: US 9,103,798 B2
(45) Date of Patent: Aug. 11, 2015

(54) MAGNETIC INSPECTION DEVICE AND METHOD

(75) Inventor: Herbert R. Weischedel, South Windsor, CT (US)

(73) Assignee: NDT Technologies, Inc., South Windsor, CT (US)

( * ) Notice: Subject to any disclaimer, the term of this patent is extended or adjusted under 35 U.S.C. 154(b) by 339 days.

(21) Appl. No.: 13/558,666

(22) Filed: Jul. 26, 2012

(65) Prior Publication Data

US 2013/0147471 A1     Jun. 13, 2013

Related U.S. Application Data

(60) Provisional application No. 61/567,808, filed on Dec. 7, 2011.

(51) Int. Cl.
    *G01N 27/82*     (2006.01)
    *G01N 27/83*     (2006.01)
    *G01N 27/90*     (2006.01)

(52) U.S. Cl.
CPC ............ *G01N 27/83* (2013.01); *G01N 27/9033* (2013.01); *G01N 27/9046* (2013.01)

(58) Field of Classification Search
CPC ... G01N 27/82; G01N 27/83; G01N 27/9046; G01N 27/9033; G01B 7/34
USPC .................................................. 324/238, 240
See application file for complete search history.

(56) References Cited

U.S. PATENT DOCUMENTS

| | | |
|---|---|---|
| 4,659,991 A | 4/1987 | Weischedel |
| 5,430,665 A | 7/1995 | Jin et al. |
| 5,804,964 A | 9/1998 | Hamelin et al. |

FOREIGN PATENT DOCUMENTS

WO        9707624 A1     2/1997

OTHER PUBLICATIONS

International Search Report for corresponding PCT Application No. PCT/US2012/068490 dated Jan. 29, 2013.

*Primary Examiner* — Reena Aurora
(74) *Attorney, Agent, or Firm* — McCormick, Paulding & Huber, LLP

(57) ABSTRACT

A magnetic inspection device and method for nondestructive testing of wire ropes and the like utilizes a leakage flux generator moveable relative to a wire rope to be inspected for inducing in sections of the wire rope magnetic flux at a saturation level. A leakage flux detector moves with the leakage flux generator, and cooperates with the leakage flux generator for detecting leakage flux at the outer surface of the wire rope saturated by the generator. The detector provides a high fidelity signal representative of the loss of metallic cross section at individual locations along the wire rope. A signal processor receiving the high fidelity signal representative of the loss of metallic cross section from the detector extracts a wire rope roughness component from the high fidelity signal.

25 Claims, 6 Drawing Sheets

Echo Cancellation (Signal Enhancement)

MAGNETIC INSPECTION DEVICE AND METHOD

CROSS REFERENCE TO RELATED APPLICATIONS

This application claims the benefit of U.S. Provisional Application 61/567,808 filed Dec. 7, 2011, the disclosure of which is incorporated herein in its entirety by reference.

FIELD OF THE INVENTION

The present invention relates to the field of magnetic inspection devices and methods. More particularly the invention relates to magnetic devices and methods for nondestructive testing of wire ropes for various forms of flaws caused by use and deterioration.

BACKGROUND OF THE INVENTION

The operating safety of cables formed by wrapped or woven wire strands, commonly referred to as wire rope, often requires that wire ropes be inspected periodically for defects. Until now rope inspections for the loss of metallic cross section (LMA) and local flaws (LF) were thought to be the proper criteria. Loss of metallic cross section measured quantitatively detects loss of wire rope cross section caused by external and internal corrosion and wear. Local flaw measurements qualitatively detect a wide variety of external and internal discontinuities such as broken wires and large scale corrosion pitting. One magnetic device for nondestructive testing of wire rope for detection of both loss of metallic cross section and local flaws is disclosed in my U.S. Pat. No. 4,659,991.

However, modern wire ropes have a tendency to deteriorate internally in more modes than previously contemplated, and the detection of all modes of external and internal deterioration has required a new approach to the nondestructive inspection of wire rope for defects.

Corrosion pitting causes stress concentrations and is extremely insidious since it causes little loss of material with rather small effects on the surface while damaging the deep structure of the metal. The pits on the wire surfaces are often covered by products of the corrosion. Corrosion pitting inhibits free movement of the wires and strands which produces additional stresses in the wires. The increased wire stresses combined with the above mentioned stress concentrations can drastically accelerate the development of fatigue breaks. Corrosion-assisted wear causes wires to corrode uniformly over their entire surface which may reduce their cross-sectional area and cause loose strands. The severity of corrosion often varies along the length of a wire rope. Frequently, corrosion is localized, but nevertheless is dangerous. The extent of corrosion is often difficult to gauge, and, as shown by experience, is usually underestimated.

Internal mechanical defects include broken wires (single and in clusters), and inter-strand nicking. Many ropes suffering from such defects are torque-balanced, multi-strand ropes comprising two or more layers of twisted strands. FIG. 1 shows a cutaway section of such wire rope. Torque-balance is achieved in multi-strand ropes by layering and wrapping inner and outer strands in opposite directions about a core. This type of rope construction limits axial rotation of a freely suspended rope under load. In addition, multi-strand ropes offer flexibility and a wear-resistant surface profile. In single fall crane operations the use of torque-balanced ropes is mandatory.

However, the strands in different layers of these ropes cross over one another at an angle and touch one another. Therefore, when multi-strand ropes bend over sheaves or a drum, they are subject to the combined effect of radial loading, relative motion between wire strands and bending stresses.

Therefore, multi-strand ropes are prone to develop inter-strand nicking as illustrated in FIG. 2 and internal wire breaks as illustrated in FIG. 3. The breaks occur primarily at the interface of the outer and immediately adjacent inner layer of strands with no externally visible signs. The wires in the inner layer typically show nicking and breaks caused by a combination of fluctuating axial wire stresses, inter-strand motions, and fluctuating radial loads. The broken wires B usually show squared-off and z-shaped ends that are typical of fatigue breaks.

In addition, many multi-strand ropes are subject to corrosive environmental conditions. For example, offshore ropes are either immersed in the sea or continually wetted by salt water spray. Heavy use in a marine environment can displace and degrade the rope lubricant. The combined effects of fatigue, corrosion, and lubricant degradation can cause rapid internal deterioration with no externally visible indications where there is no effective form of protection. Since deterioration of torque-balanced rope is not easily detected, failure of the rope is often unexpected.

Similar nicking and fatigue patterns occur in IWRC (Independent Wire Rope Core) ropes. FIG. 4 shows a typical cross-section diagram of such a rope. For IWRC ropes, the wires of the outer strands of the outer wire bundles have a larger diameter than the outer wires of the core. To minimize inter-strand nicking between the outer strands and the IWRC core, the ropes are designed such that the wires of the outer strands and of the core are approximately parallel. This parallel arrangement is usually achieved by a Lang lay construction for the core and an ordinary lay construction for the outer strands.

The result of these geometrical features is that under fluctuating tensile loads the outer IWRC wires are continuously forced into the valleys between the outer wires, and are then released. The mechanism results in secondary bending stresses which lead to large numbers of cores with broken wire strands due to fatigue breaks. The breaks can be very close together and thus form groups of breaks. Eventually, the IWRC can break, or it can completely disintegrate into short pieces of wire about a half lay length long. This condition is commonly called complete rope core failure.

As the IWRC core fails, the outer strands lose the radial support. The lack of support allows the outer strands to bear against each other tangentially. The resulting inter-strand nicking restricts the movement of the strands within the rope. Without the freedom of movement, secondary fatigue breaks in the wires of the outer strands in the strands of the outer bundles will develop at the strand points of tangency. Because the fatigue breaks develop in the valleys between the outer strands, they are called valley breaks.

As another example, spiral strand is made up of concentric layers of wires spirally wound in opposite directions to allow a measure of torque balance. The individual wires in different layers touch locally and at an angle, and the helical geometry within the layers creates radial inter-layer contact forces. When used in mooring applications, spiral strands are subject to fluctuating loads, and especially bending. Depending on the level of axial tension and radius of curvature, spiral strands are subject to interlayer slippage, which causes axial motion between wire strands in different layers combined with tension and torque stresses. Therefore, it is expected that as a result of the geometrical features, wire strands of layers will develop inter-strand nicking and fretting, and eventually, secondary fatigue breaks.

In view of the numerous ways in which wire ropes can fail both externally and internally, it is desirable to be able to inspect or non-destructively test the ropes in both areas. Loss of metallic cross section is certainly one form of inspection that reveals a general weakening of the wire rope due to external wear. External wear can be detected visually, but this type of inspection is limited generally to the outer most portion of the wire rope. Deeper internal inspection is therefore most important. Unfortunately internal inspection techniques for the defects described above are somewhat lacking and need to be more quantitative to provide a more reliable indication of rope safety. It is accordingly an object of the present invention to provide a non-destructive device and method of inspecting wire rope for assessing rope condition externally and internally at a quantitative level.

SUMMARY OF THE INVENTION

For purposes of the present invention, the following definitions are given.

Basic Loss of Metallic Cross-Sectional Area (BLMA)—is defined as the loss of metallic cross-sectional area that stays substantially constant and smooth over limited distances, typically equal to or greater than one lay length along a length of wire rope. Lay length, also sometimes referred to as the pitch length, is the length of wire rope along the rope axis in which a wire strand makes one complete revolution or wrap about the axis. While the BLMA is mostly a theoretical concept, for actual ropes this type of defect is usually caused by wear and corrosion-assisted wear.

Wire Rope Roughness (WRR)—is the aggregate surface roughness of all wires in a rope at one section of a rope. Typically WRR varies considerably and rapidly, that is, at high spatial frequencies, over short lengths of rope of less than one lay length. WRR includes rope deterioration caused by corrosion pitting, broken wires and clusters of broken wires, inter-strand wear and nicking. Consequently, WRR can be a more accurate quantitative measure of the internal wire rope structure and condition.

The present invention relates to a magnetic inspection device for nondestructive testing of wire ropes and the like. The device has a leakage flux generator moveable relative to a wire rope to be inspected for inducing in sections of the wire rope magnetic flux at a saturation level. A leakage flux detector moves with and cooperates with the leakage flux generator for detecting leakage flux at the outer surface of the wire rope saturated by the generator. The detector provides a high fidelity signal generally representative of the loss of metallic cross section at individual stations along the wire rope. A signal processor receives the high fidelity signal from the detector and extracts a wire rope roughness component from the high fidelity signal.

The flux generator generally has strong magnets with magnetic poles positioned at longitudinally spaced stations along the rope to induce a magnetic field in a segment of the rope at a saturation level. Then saturation leakage flux appears at the surface of the rope. The leakage flux varies with changes in the loss of metallic cross section of the wire rope, but on a micro-scale the loss of metallic cross-section can be broken down into the basic loss of metallic cross-section (BLMA) component and a wire rope roughness (WRR) component. The breakdown of the signal from the leakage flux detector into the two components is performed by the signal processor. It is important to retain a high fidelity signal of the leakage flux since the WRR component can be a rapidly changing and relatively small component of the leakage flux signal.

The present invention also relates to a method of inspecting a wire rope and the like for defects. The method comprises the steps of inducing in the axial direction of a section of wire rope a magnetic flux at a saturation level, and moving the magnetic flux and the wire rope relative to one another to cause the magnetic flux to pass through different sections of the wire rope. The method further includes the steps of detecting leakage flux from the magnetic field at the surface of the wire rope during relative movement by means of a flux sensor and producing a flux signal representative of the change of leakage flux. The flux signal is then processed to extract a WRR component representative of wire rope roughness and a BLMA component representative of the basic loss of metallic cross section of the wire rope. Since the wire rope roughness signal can be a rapidly changing and is a relatively small component of the leakage flux signal, it is important to detect the changes in leakage flux with high fidelity and not suppress the high frequency variations.

DESCRIPTION OF THE PREFERRED EMBODIMENTS

Figure 1:
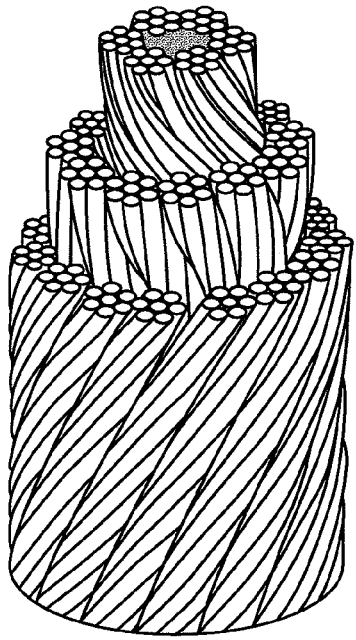
FIG. 1 shows a cutaway view of a multi-strand wire rope providing a torque balanced design.
Figure 2:
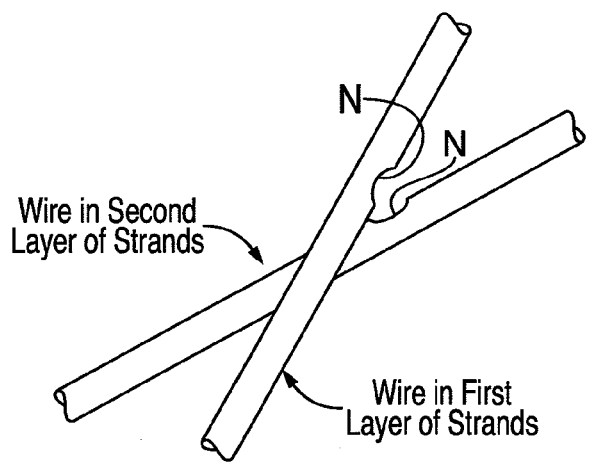
FIG. 2 shows nicking and wear where two wire strands in a wire rope cross over one another.
Figure 3:
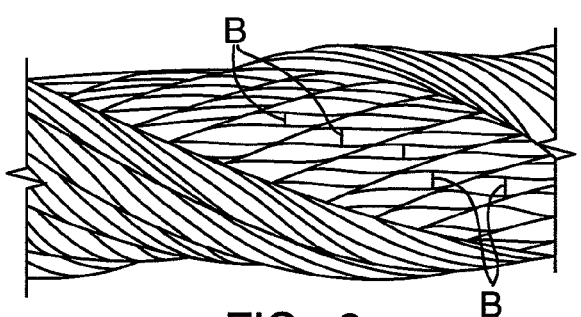
FIG. 3 shows a wire rope partially cut away to reveal broken wires in the second layer of strands.
Figure 4:
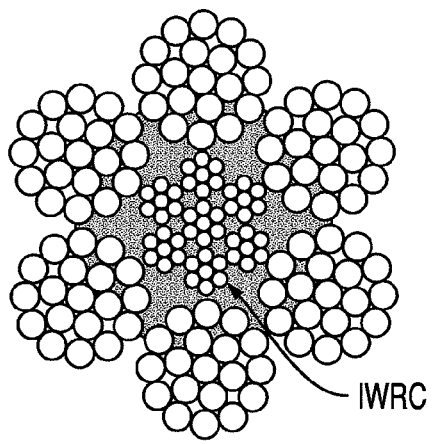
FIG. 4 is cross-section of a wire rope having an independent wire rope core (IWRC).
Figure 5:
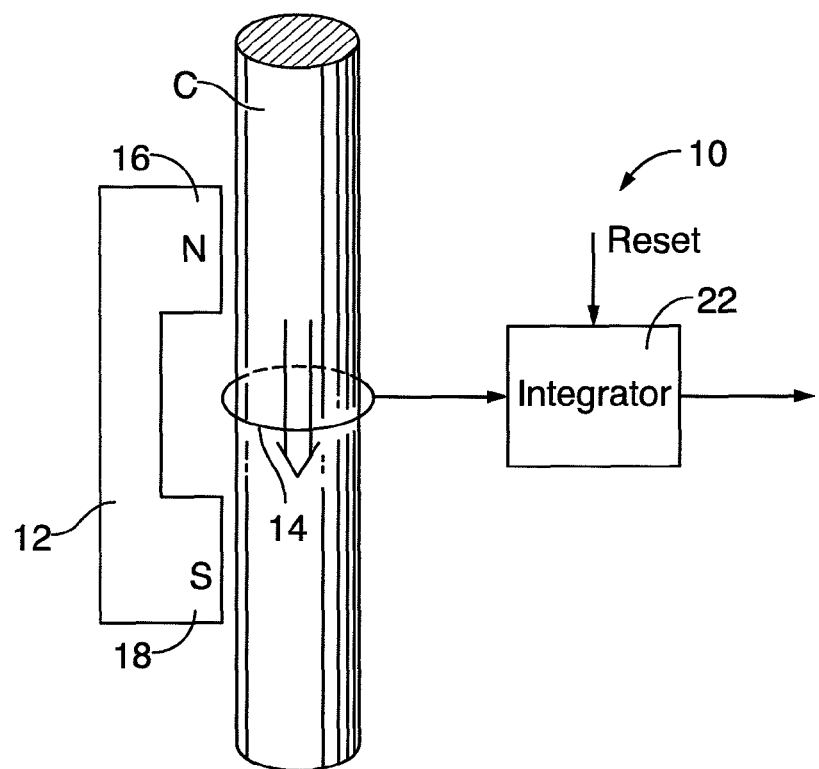
FIG. 5 is a simplified schematic illustration of a flux generator, flux detector, and signal conditioning of the present invention.

A magnetic inspection device 10 having a flux generator 12 and a flux detector 14 for inspecting wire rope or cable C in accordance with the present invention is illustrated schematically in FIG. 5. The flux generator 12 is a large permanent magnet with opposite poles 16, 18 positioned at spaced stations along the rope C. The flux detector 14 may be a series of Hall sensors, but is preferably a sensing coil of conductive wire with a large number turns circumscribing the rope to produce a detectable signal from currents induced by leakage flux at the surface of the rope. The inspection device 10 and wire rope C are movable relative to one another to allow the flux generator 12 to induce a magnetic field at a saturation level in a longitudinal section of the rope lying between the opposite poles 16, 18 of the generator, while the flux detector 14 senses the variation in leakage flux at the outer surface of the rope. The leakage flux varies with the loss of metallic cross-section and local faults such as broken wire strands, corrosion, and pitting or nicking of the wires. The signal from the flux detector 14 represents the changes in flux due to all the faults, such as loss in metallic cross-section and broken wires in the rope.

The relative movement of the inspection device 10 and the rope C during an inspection of the wire rope C can be caused by movement of the rope, movement of the inspection device, or both. As an example, inspection of an elevator cable is most easy accomplished by holding the inspection device stationary while the cable passes through the device. On the other hand, a bridge suspension cable must be inspected by moving the inspection device along the cable by means of a traction device or tow ropes.

When the magnetic inspection device 10 moves relative to the wire rope C, the changes in leakage flux in the rope induce currents in the sensing coil 14. The current signal is processed through an integrator 22 that converts the signal into a signal representative of the total loss of metallic cross-section, or the total LMA signal.

Figure 6:
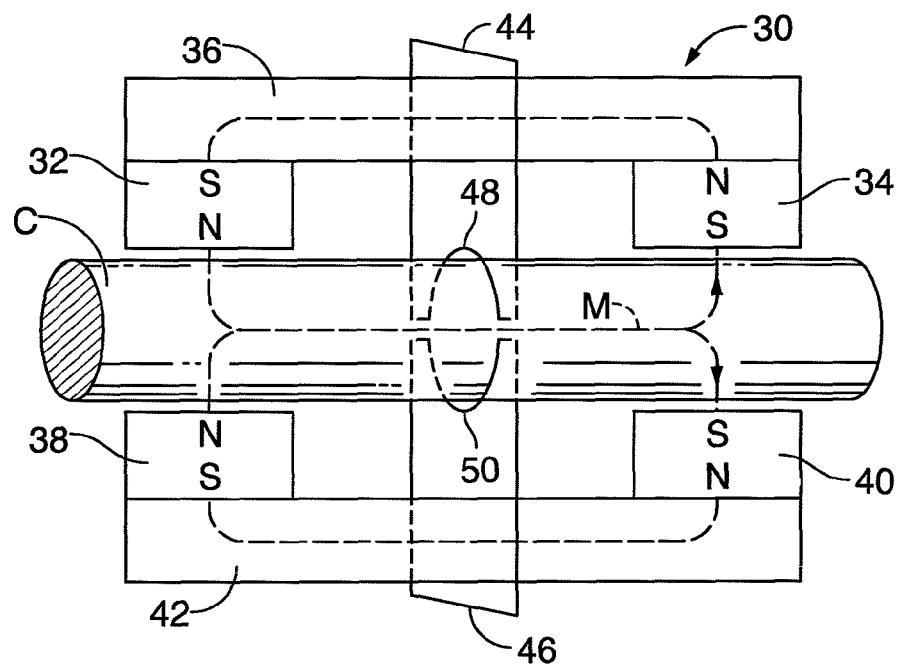
FIG. 6 is a schematic illustration of a flux generator and flux detector in a bifurcated configuration.

A preferred embodiment of the magnetic inspection device 30 is shown schematically in FIG. 6. The device is comprised by a bifurcated flux generator having two bifurcations positioned at opposite sides of the wire rope C for mounting on and removal from the wire rope at midpoints of the rope. One bifurcation is comprised by two magnets 32, 34 generally conforming to the surface of the rope and joined serially with opposite ends of a ferromagnetic bar 36 in a magnetic circuit including the rope. The other bifurcation is similarly constructed with two magnets 38, 40 generally conforming to the surface of the rope and joined serially by a ferromagnetic bar 42 in another complementary magnetic circuit through the rope. The two bifurcations may be coupled together by hinges with like poles of the magnets disposed in adjacent relationship for inducing magnetic flux in a section of the wire rope at a saturation level.

The flux detector in the magnetic inspection device 30 is also bifurcated and is comprised by a first coil 44 interlaced with the magnetic circuit passing through the ferromagnetic bar 36, and a second coil 46 in the same plane as the first coil and interlaced with the magnetic circuit passing through the ferromagnetic bar 42. The first coil 44 is a multi-turn coil having one section 48 conforming closely to one portion of the outer surface of the wire rope C. The second coil 46 is also a multi-turn coil having one section 50 conforming closely to the other portion of the outer surface of the wire rope C. The two conforming coils detect leakage flux around substantially the full circumference of the rope, and together provide a signal to the signal processor for processing as defined further below. For further description of the bifurcated flux generator, the flux detectors and their operation, reference is made to my U.S. Pat. No. 4,659,911.

Figure 7:
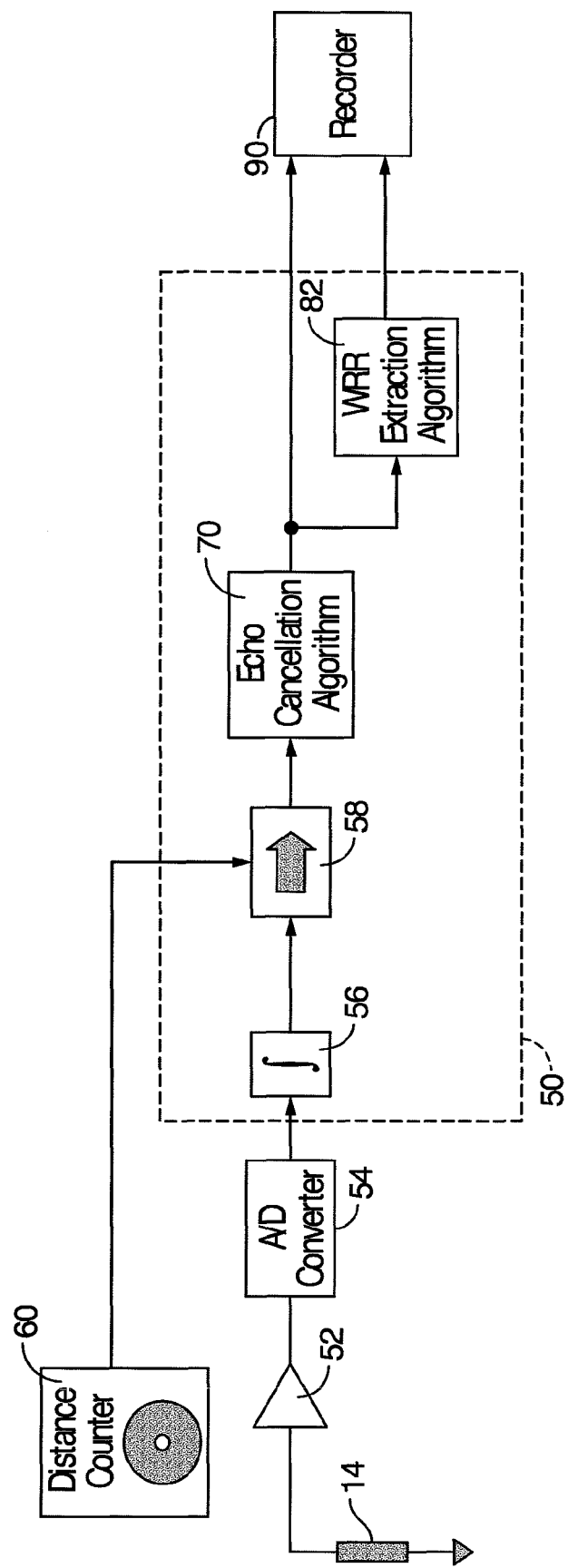
FIG. 7 is a schematic diagram of a signal processor of the present invention.

FIG. 7 illustrates the flux detector 14 and the associated signal processor 50 for extracting a wire rope roughness (WRR) signal from the total LMA signal provided by the detector. It should be understood that the flux detector may comprise one or more complementary detectors, such as the coils 44, 46 in FIG. 6 whose signals are combined as described in U.S. Pat. No. 4,659,991 to provide a signal representative of the total loss of metallic cross-section at each station along the wire rope C. The signal from the detector is typically an analog signal and is conditioned for further processing in the signal processor 50 by a preamplifier 52 and then converted by an analog-to-digital converter 54 to digital form in the processor.

Since flux detectors in the form of coils only detect changes in leakage flux at the surface of the wire rope, the detector signal is integrated by integrator 56 to obtain a total LMA signal representative of total flux or loss of metallic cross-sectional area upon entry into the signal processor 50. The signal from the flux detector is a time-based signal, and in order to attach the signal at any given time to a station of the wire rope, the signal is converted to a distance-based signal by a time/distance converter 58 that receives a rope displacement or position signal from a distance counter 60. Therefore, the total LMA signal emanating from the converter 58 can be correlated with the various stations along the wire rope.

Since wire roughness is a fraction of the total loss of metallic cross-section of a wire rope and varies at a high frequency as the detector moves along a rope, it is important that the fidelity of the flux signal from the detector 14 not be destroyed or compromised by filtering, low-pass or otherwise, normally used to improve signal-to-noise ratios.

Figure 8:
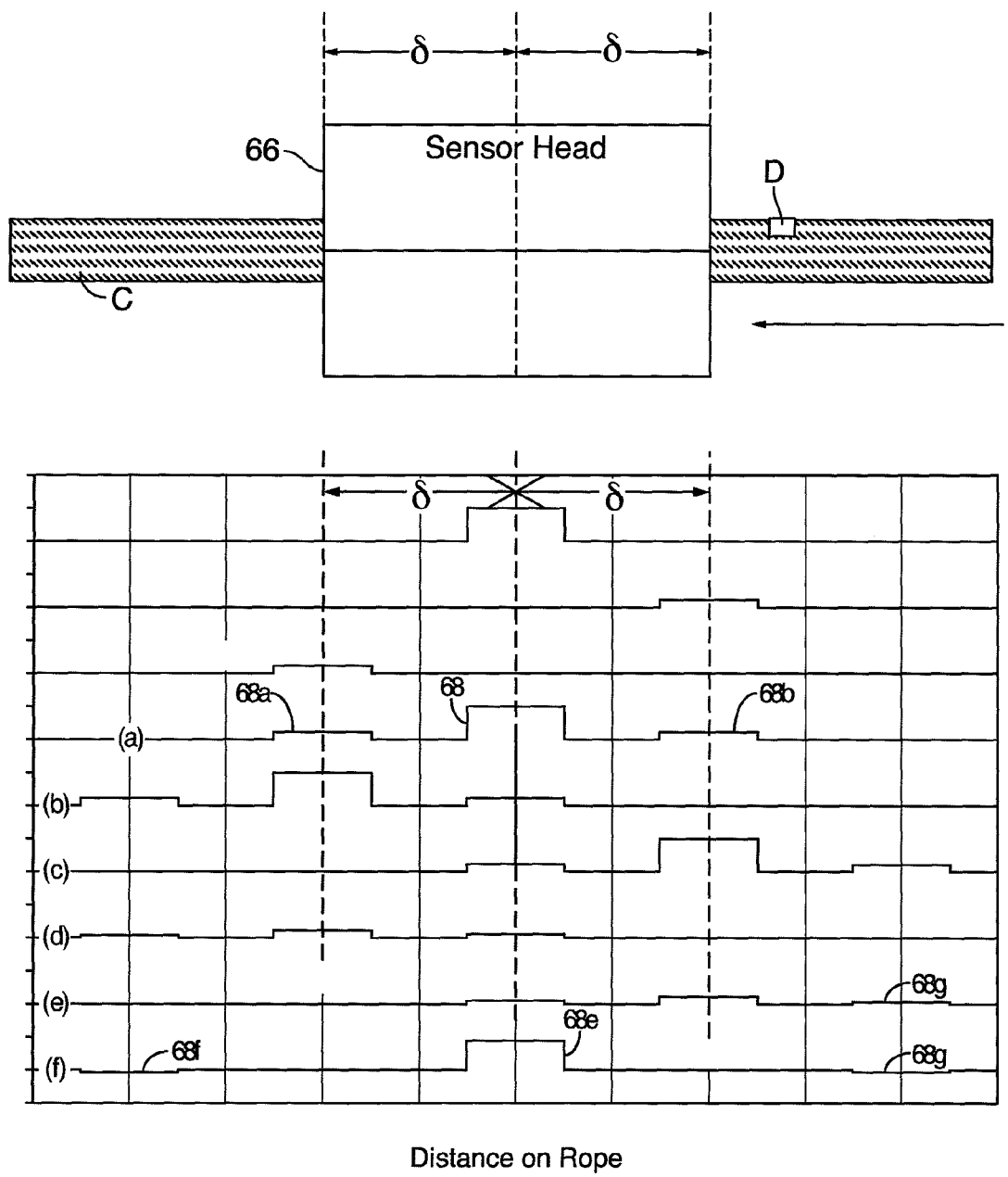
FIG. 8 is a schematic illustration of a flux detector head and wire rope with a defect and graphs of the detector signal arising from the defect.

Furthermore, it is desirable to remove from the total LMA signal, as much as possible, artifacts that are introduced by the geometry of the detector. One such artifact that is noticeable from many detector heads is an echo such as illustrated with the aid of FIG. 8. FIG. 8 illustrates the wire rope C passing through the envelope of a detector head 66 that could have the construction of the detector shown in detail in FIG. 6. FIG. 8 also includes distance-based graphs of the detector signal at various stages of processing. The graph (a) is correlated graphically with the various stations of the wire as the wire moves through the head.

Assuming the detector head 66 has an overall length 28 along the rope C, when a defect D, such as a broken wire, passes through the head, a primary signal 68 occurs when the defect passes the detector coils at the center of the head, an echo signal 68a when the defect enters the head, and an echo signal 68b when the defect leaves the head. The echo signals are characteristic of the sensor geometry, and are artifacts that must be reduced in significance in the LMA signal to obtain an unadulterated wire roughness signal.

Figure 9:
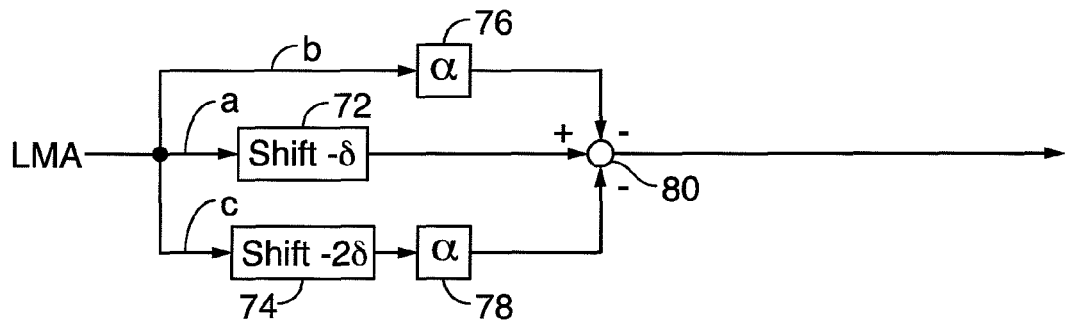
FIG. 9 is a functional block diagram of the echo cancellation algorithm.

The echo signals 68a and 68b can be reduced to insignificance by a software algorithm 70 shown in the signal processor 50 of FIG. 7, or equivalent hardware. FIG. 9 is a functional diagram of either the hardware or software solution. The total LMA signal with echoes from the converter 58 is fed through three paths to a summing junction 80. The first path without a shift register includes an amplifier 76 that reduces the signal amplitude by a factor $\alpha$, such as 0.25, a fraction characteristic of a given detector head and which generally corresponds to the ratio of the amplitudes of echo signal 68a or 68b to the primary LMA signal 68. The graph (b) in FIG. 8 illustrates the LMA signal prior entering the amplifier 76. The two paths containing the shift registers 72, 74 produce time-shifted facsimiles of the LMA signal shown respectively in graph (a) and graph (c) in FIG. 8. The shift register 72 delays the signal by the distance $\delta$ relative to the LMA signal in graph (b) to produce the graph (a), and the shift register 74 delays the signal by the distance 2 $\delta$ relative to the LMA signal in graph (b) to produce the signal of graph (c). Both shifted signals are then scaled in a multiplier 76 or 78 by the factor $\alpha$, which reduces the amplitude of the primary signal 68 to the amplitude of the echo signals 68a, 68b, and the amplitude of the echo signals to insignificant values. The scaled signals are shown in graphs (d) and (e) of FIG. 8.

As indicated in FIG. 9, the scaled and time-shifted signals are then subtracted from the total LMA signal at the summing junction 80 which causes the scaled echo signals 68a, 68b to essentially be insignificant in an enhanced LMA signal at the output of the summing junction as illustrated in graph (f) of FIG. 8. As shown, the enhanced LMA signal of graph (f) has a slightly attenuated primary signal 68e and mere vestiges 68f, 68g of the echo signals. If the vestiges 68f, 68g were significant the enhanced LMA signal could be processed a second time through another algorithm such as shown in FIG. 9 for a further reduction in significance.

The enhanced LMA signal produced by the echo cancellation algorithm 70 contains clearly delineated defects without perceptible echoes, and is one output of the signal processor 50 as shown in FIG. 7. The enhanced signal is also fed to a WRR extraction algorithm 82 for extracting the WRR component from the LMA signal. The extraction of the WRR component is accomplished by determining the basic LMA signal, that is, the BLMA signal attributed to large scale loss of metallic cross-section arising from wear, abrasion, large scale corrosion, and wire breakage, and then subtracting the BLMA signal from the enhanced LMA signal. The resultant is the wire rope roughness (WRR) component.

Figure 11:
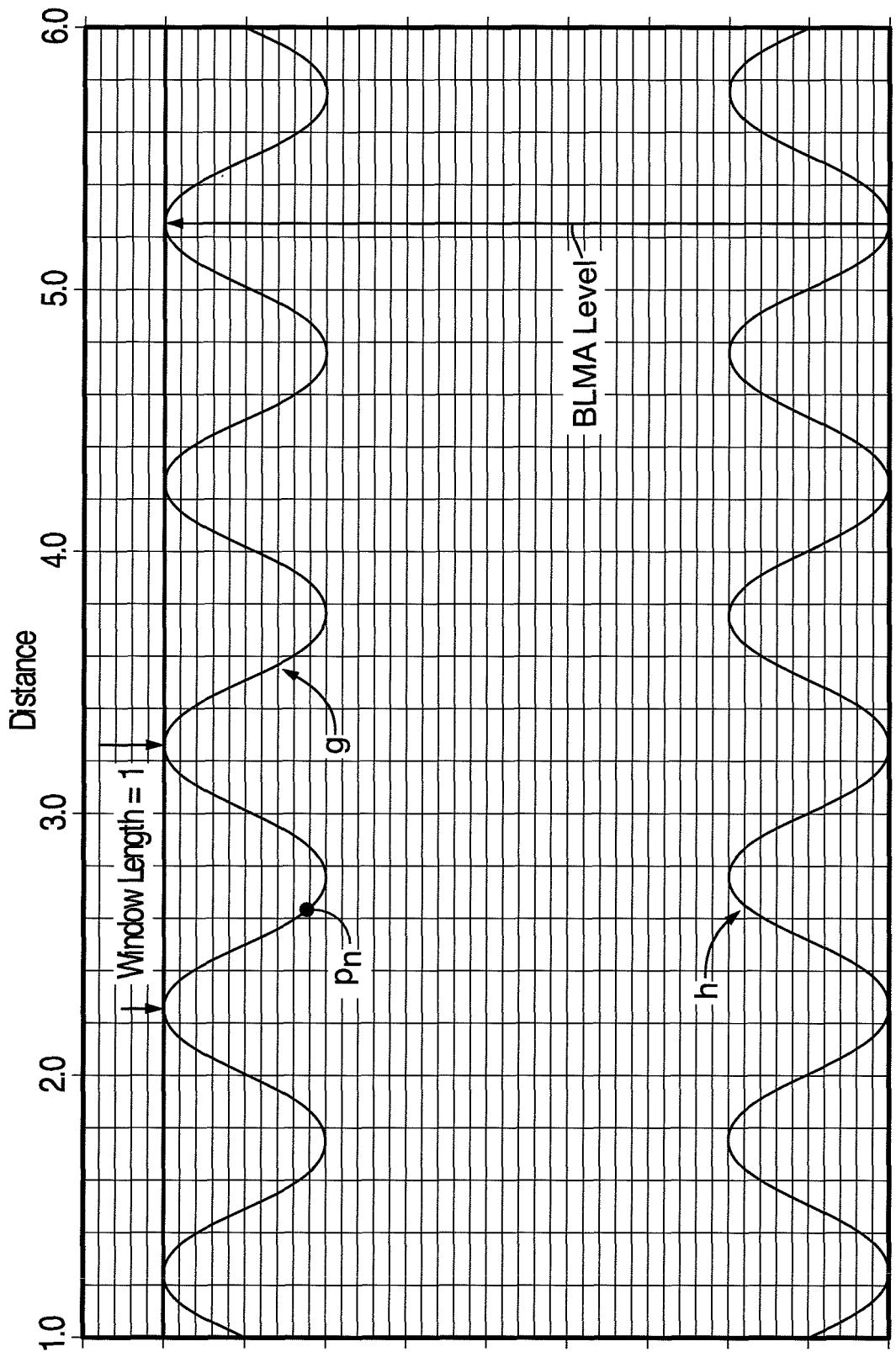
FIG. 11 is a graphic illustration of the total detector signal and the extracted WRR signal.

The extraction process is perhaps best illustrated by the enhanced LMA signal in the graphs of FIG. 11. The graph (g) illustrates the magnitude of the enhanced LMA signal. The BLMA component is a relatively steady or slowly varying component representative of large scale loss of metallic cross-section. The BLMA component does not vary considerably over lengths of the wire rope equal to or less than the lay length L. The WRR component varies at a much higher rate or frequency than the BLMA component, and hence is the reason conventional low pass filters can not be used in processing the LMA signal. In the graph (g) in FIG. 11 BLMA signal can be assumed to be the signal level at the base of the sinusoidal curve, and the sinusoidal portion of the graph (g) represents the high frequency WRR component.

Figure 10:
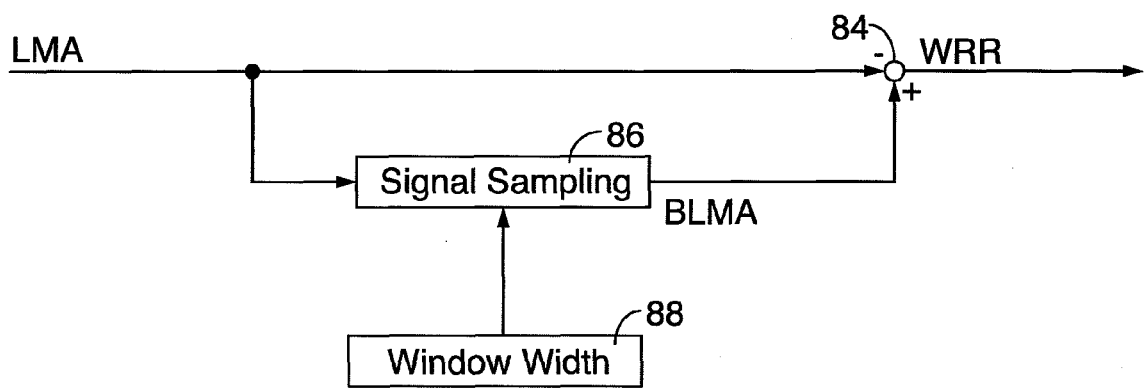
FIG. 10 is a functional block diagram of the WRR extraction algorithm.

FIG. 10 illustrates the WRR extraction subroutine 82 in detail. The enhanced LMA signal passes to the summing junction 84 as a subtrahend, and also passes to an algorithm 86. The algorithm extracts the BLMA component and then feeds the BMLA component to the summing junction 84. When the enhanced LMA signal is subtracted from the BLMA component, the resultant output of the junction 84 is the WRR component. Hence the subroutine 82 acts as a high pass filter that ensures a WRR signal without distorting the original wave shape. The enhanced LMA signal, the BLMA signal and the WRR signal can be recorded in a graphical or other recorder 90 in FIG. 7.

The determination of the BLMA component without distortion is important for an accurate determination of the WRR component. Hence the algorithm 86 in a preferred embodiment uses a signal sampling technique. The enhanced LMA signal in digital form has discrete values at each point $p_n$ along the length of the rope. The algorithm takes a sampling of the values in a window spanning a point $p_n$ at each side as illustrated in FIG. 11. The length of the window can be selected through the input 88, and generally is selected to span a length of rope not less than the lay length L. The algorithm 86 then searches for the maximum value in the window of values, and assigns the maximum value as the BLMA value for the spanned point $p_n$. As the algorithm 86 processes the enhanced LMA signal, the window moves along the rope from point to point and assigns a BLMA value to each point $p_n$. In this manner the value of the BLMA component is established for each point $p_n$. Upon subtracting the values of the enhanced LMA signal from the BLMA signal at summing junction 84 point for point, the WRR component is extracted. The WRR component obtained in this fashion is illustrated by the graph (h) in FIG. 11.

It will be understood that the present invention has been described in a preferred embodiment, and the invention can be utilized in numerous other forms. For example, the flux detector can be formed from other types of detectors such as Hall sensors rather than coils with suitable processing of the sensor signals to extract the WRR component of flux. Certain flux sensor heads may produce the total LMA signal without artifacts, and supplemental enhancement to eliminate the artifacts may not be necessary. The processing of the total LMA signal to extract the WRR component may use analog hardware or digital software in a variety of forms. Accordingly, the present invention has been described in a preferred embodiment by way of illustration rather than limitation.

The invention claimed is:

1. A magnetic inspection device for nondestructive testing of wire ropes and cables formed by wrapped or woven wire strands comprising:
   a leakage flux generator moveable relative to a wire rope to be inspected for inducing in sections of the wire rope magnetic flux at a saturation level;
   a leakage flux detector moveable with and cooperating with the leakage flux generator for detecting leakage flux at the outer surface of the wire rope saturated by the generator, the detector providing a high fidelity signal representative of the total loss of metallic cross section at individual locations along the wire rope; and
   a signal processor receiving the high fidelity signal representative of the total loss of metallic cross section from the detector and extracting a wire rope roughness component from the high fidelity signal.

2. A magnetic inspection device as defined in claim 1 wherein the signal processor processes the high fidelity signal representative of a total loss of metallic cross section of the wire rope, and includes a signal extractor separating the signal into a basic loss of metallic cross section component and a component representative of wire rope roughness.

3. A magnetic inspection device as defined in claim 2 wherein the leakage flux detector includes a coil having at least one portion of the coil disposed in close proximity to the surface of a wire rope during inspection for sensing leakage flux at the surface.

4. A magnetic inspection device as defined in claim 2 wherein the signal extractor includes:
   a signal sampling component receiving the total loss of metallic cross-section signal and deriving a signal representative of a basic loss of metallic cross section component along the length of a wire rope; and
   a signal subtracting component receiving the total loss of metallic cross-section signal and the signal representative of basic loss of metallic cross-section component for extracting a wire rope roughness component from the high fidelity signal.

5. A magnetic inspection device as defined in claim 4 wherein the total loss of metallic cross-section signal is a digital signal comprised of digital values of flux at given stations along the wire rope, the sampling component produces digital values of the basic loss of metallic cross-section component at the given stations, and the extractor subtracts the basic loss of metallic cross section values from the total loss signal at corresponding stations along a wire rope to obtain the values of the wire rope roughness component at the given stations.

6. A magnetic inspection device as defined in claim 4 wherein the signal sampling component derives the basic loss of metallic cross section values from the high fidelity signal at discrete stations along a wire rope by selecting the maximum value of the signal within a window of values straddling each discrete station.

7. A magnetic inspection device as defined in claim 6 wherein the window has a length along a wire rope approximately equal to the lay length L of a wire rope.

8. A magnetic inspection device as defined in claim 1 further including a graphical recorder to record the wire rope roughness along a length of a wire rope.

9. A magnetic inspection device as defined in claim 1 wherein:
the leakage flux generator includes magnet means comprised of two or more magnets having two opposite magnetic poles spaced from one another for positioning at spaced stations along a wire rope and for movement relative to the wire rope, the magnet means having a strength sufficient to generate in the wire rope between the spaced stations magnetic flux at the saturation level; and
the leakage flux detector is positioned between the opposite magnetic poles of the magnet means for movement with the magnet means relative to the wire rope.

10. A magnetic inspection device as defined in claim 1 wherein:
the magnet means is divided into two bifurcations for mounting on and removal from a wire rope, each bifurcation having two spaced and magnetically opposite poles and like poles of the bifurcations disposed in adjacent relationship for inducing magnetic flux in a section of the wire rope;
the leakage flux detector is comprised of at least two sensors, one sensor being associated with one bifurcation and the other sensor being associated with the other bifurcation; and
the signal processor receiving the high fidelity signal from the sensors includes an echo suppressor suppressing echo artifacts in the high fidelity signal originating from the two sensors.

11. A magnetic inspection device as defined in claim 10 wherein the echo suppressor in the signal processor receives and processes the high fidelity signal from the sensors to suppress echo artifacts prior to the extraction of the wire rope roughness component from the high fidelity signal.

12. A magnetic inspection device as defined in claim 10 wherein:
the signal processor includes a time/distance converter converting the high fidelity signal produced by the coils to a distance-referenced signal correlated with stations along the wire rope; and
the echo suppressor receives the distance-referenced signal from the converter and includes signal shifting capacity for removing the echo artifacts from the high fidelity signal based upon the geometry of the sensors.

13. A magnetic inspection device as defined in claim 10 wherein the sensors include at least one coil interlaced with the magnetic flux generated by one of the bifurcations, and at least another coil interlaced with the magnetic flux generated by the other of the bifurcations.

14. A magnetic inspection device for nondestructive testing of wire rope for loss of metallic cross section and local flaws, comprising:
a bifurcated flux generator having two bifurcations for generating flux in a wire rope at a saturation level, each bifurcation having a magnet consisting of two magnetic poles, the poles of the magnets in each bifurcation having like spacing so that the bifurcations can be positioned in straddling relationship with a wire rope and can be moved relative to a wire rope with like poles of the magnets in opposed relationship to induce magnetic flux in sections of a wire rope between the poles;
flux detectors associated respectively with the two bifurcations, the detectors sensing the changes in flux at the surface of a wire rope as the bifurcations and wire rope move relative to one another and producing a total flux signal;
a signal processor receiving the total flux signal from the flux detectors and extracting a loss of metallic cross section component and a wire roughness component from the total flux signal.

15. A magnetic inspection device as defined in claim 14 wherein:
the signal processor includes a basic loss of metallic cross-section signal extractor deriving from the total flux signal a basic flux signal as a measure of the basic loss of metallic cross section component at specified stations of a wire rope;
and a subtractor subtracting the basic flux signal from the total flux signal at the specified stations as a measure of the wire roughness at the specified stations.

16. A magnetic inspection device as defined in claim 15 wherein the total flux signal is a digital signal designating the total flux at individual station of the wire rope, the signal processor operates the total flux signal in digital form to cause the signal extractor and the subtractor to perform the averaging and subtracting operations at multiple stations of a wire rope as the rope and bifurcations move relative to one another.

17. A magnetic inspection device as defined in claim 16 further including a wire rope distance counter providing a tracking signal indicative of the station of a wire rope being inspected; and the signal processor includes a time/distance converter receiving the total flux signal and the tracking signal to correlate the total flux signal from the flux detectors with given stations along a wire rope.

18. A magnetic inspection device as defined in claim 14 wherein the flux detectors are coils sensing the rate of change of leakage flux at the surface of a wire rope moving relative to the bifurcations, and the signal processor further includes an integrator processing the flux signals.

19. A method of inspecting a wire rope and cables formed by wrapped or woven wire strands for defects comprising:
inducing in the axial direction of a section of wire rope a magnetic flux field at a saturation level;
moving the magnetic field and the wire rope relative to one another to cause the magnetic flux field to pass through different sections of the wire rope;
detecting leakage flux from the magnetic field at the surface of the wire rope during relative movement by means of a flux sensor and producing a flux signal representative of the change of leakage flux; and
processing the flux signal to extract a component representative of wire rope roughness and a component representative of the basic loss of metallic cross section of the wire rope.

20. A method of inspecting a wire rope as defined in claim 19 wherein the step of processing is performed continuously during the step of moving to obtain measures of the wire rope roughness and loss of metallic cross section of the wire rope along multiple sections of the wire rope.

21. A method of inspecting a wire rope as defined in claim 19, wherein the processing of the flux signal includes:
determining from the detected flux signal a basic flux signal representative of the basic loss of metallic cross section at a selected station of the wire rope; and
subtracting the basic flux signal from the detected flux signal at the selected station to yield the wire rope roughness signal at the selected station.

22. A method of inspecting a wire rope as defined in claim 21 wherein the step of determining the basic flux signal comprises determining the maximum value of the detected flux in a window of values along the wire rope spanning the selected station.

23. A method of inspecting a wire rope as defined in claim 19 wherein:
   the step of detecting leakage flux includes using coils to generate signals representative of the change in leakage flux at the surface of a wire rope; and
   the step of processing includes integrating the signals representative of the change in leakage flux.

24. A method of inspecting a wire rope as defined in claim 23 including the step of using a wire rope distance counter to correlate the detected loss of metallic cross section and wire rope roughness components with specific stations of the wire rope.

25. A method of inspecting a wire rope as defined in claim 19 including the step of using a wire rope distance counter to correlate the detected loss of metallic cross section and wire rope roughness components with specific stations of the wire rope.

\* \* \* \* \*